United States Patent [19]

Chapelet et al.

[11] 4,191,702

[45] Mar. 4, 1980

[54] PREPARATION OF ALKYL OR ARALKYL THIOSULFATES

[75] Inventors: Gilbert Chapelet, Bron; Patrice Lubin, Meusnes; Robert Nouguier, Plan de Cuques, all of France

[73] Assignee: Elf Union, Paris, France

[21] Appl. No.: 951,521

[22] Filed: Oct. 16, 1978

[30] Foreign Application Priority Data

Oct. 11, 1978 [FR] France .................................. 77 30979

[51] Int. Cl.² ........................................... C07C 153/07
[52] U.S. Cl. .............................................. 260/453 RY
[58] Field of Search ................................. 260/453 RY

[56] References Cited

U.S. PATENT DOCUMENTS

| | | | |
|---|---|---|---|
| 2,892,861 | 6/1959 | Doerr et al. | 260/453 RY |
| 3,153,077 | 10/1964 | Tesoro | 260/453 RY |

*Primary Examiner*—Alan L. Rotman
*Assistant Examiner*—Robert C. Whittenbaugh
*Attorney, Agent, or Firm*—Burgess, Ryan and Wayne

[57] ABSTRACT

Process for obtaining alkyl- and arylalkylthiosulfates in a water-organic solvent two-phase system by nucleophilic substitution of the halogen of an alkyl or arylalkyl halide by a thiosulfate ion, characterized by the fact that the substitution is effected in the presence of a phase transfer agent acting as a catalyst and used in catalytic proportions.

14 Claims, No Drawings

PREPARATION OF ALKYL OR ARALKYL THIOSULFATES

The preparation of alkyl or arylalkyl thiosulfates by nucleophilic substitution of a halide with a thiosulfate ion according to the reaction $$RX + S_2O_3^{--} \rightarrow R-S_2O_3^- + X^-$$

was discovered by Bunte in 1874. B. Milligan and J. M. Swan (Reviews of Pure and Applied Chemistry 12:72, 1962) have improved the experimental conditions through the use of a third solvent such as ethanol.

This third solvent represents a cumbersome factor for various reasons, such as additional cost and decrease of the useful capacity of the reactor; and finally these thiosulfates are water-soluble synthetic intermediates: any reaction with these products yields a substance that is soluble in an organic medium; hence to avoid extraction losses at the end of the reaction chains the ethanol must be removed.

A simple method conceivable for effecting this reaction may consist in the use of a phase transfer agent permitting the nucleophilic group ($S_2O_3^{--}$) to pass from the aqueous into the organic phase in which the substitution reaction takes place. However, in view of the monoanionic nature which is very specific of the product obtained, it can be expected that the phase transfer agent remains associated with this anion in the form

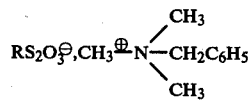

and that it acts only when present in stoichiometric quantity. Indeed J. Dockx, Synthesis 8:441, 1973, has demonstrated the existence of such catalyst poisonings during the substitution of iodides.

The process forming the subject of the present invention makes it possible to avoid these poisonings by carrying out the nucleophilic substitution of an alkyl or aralkyl halide by a thiosulfate ion in the presence of a phase transfer agent, with the latter acting in a catalytic amount, i.e. in an amount of 0.5 to 10 mole percent, and more particularly 2 to 10 mole percent.

The term "phase transfer agent" is understood to mean, in a nonlimitative manner, the aforementioned ammonium and phosphonium salts described by Dockx, or those described by E. V. Dehmlow, Angewe. Chem. Intern. Ed. 13(3):170, 1974, such as trimethylbenzylammonium chloride, triethylbenzylammonium chloride, tricaprylmethylammonium chloride, trihexylmethylammonium chloride, cetyltrimethylammonium chloride, tributylhexadecyl phosphonium bromide, dimethylphenyldodecylammonium chloride, etc.

Finally, ion exchange resins on which the quaternary ammonium compounds are grafted may be used as phase transfer agents.

The alkyl and/or aryl halides serving as starting materials in the reaction with sodium thiosulfate have the general formula R—X, wherein, R may be a saturated or unsaturated alkyl group having 2 to 25 carbon atoms, such as the allyl, butyl or hexadecyl group;

R may be an aryl group such as the benzyl group;

R may also be an ester group and X is a halogen, preferably chlorine or bromide.

Finally the reaction extends to dihalides of the formula X—R—X wherein X and R have the same meaning as above.

The mode of operation of the synthesis of the alkyl and aralkyl thiosulfates consists in (a) dissolving 1.2 equivalents of sodium thiosulfate in 0.03 to 0.15 liter of demineralized or distilled water;

(b) dissolving 1 equivalent of halide in 0.2 to 0.5 liter of an aromatic or saturated organic solvent;

(c) adding 0.02 to 0.1 molar equivalent of the phase transfer agent to the mixture of the above two solutions;

(d) refluxing for 2 to 24 hours depending on the nature of the halide, the mixture being agitated while a gentle current of nitrogen is bubbled through;

(e) identifying the alkyl or aralkyl thiosulfates formed, which are in the presence of sodium sulfate, the transfer agent and the unreacted halide, if any.

Table I compiles the nonlimitative examples of the synthesis carried out in accordance with the invention and described below.

In this table, "unreacted R=X" represents the halide which has not reacted even after the identification step;

t is the duration of the reaction $RX + S_2O_3^{--}$;

the % of catalyst refers to mole percent based on the moles RX $S_2O_3^{--}$ is used in a 20% molar excess relative to the halide;

the % of $RSSO_3^-$ gives the degree of advance of the reaction $RCl \rightarrow RSSO_3^-$;

the "complement to 100% represents the halide which has not reacted after this reaction.

EXAMPLE I 1.2 equivalents of sodium thiosulfate are dissolved in 0.15 liter of demineralized or distilled water. In a separate operation 1 equivalent of allyl chloride is dissolved in 0.2 liter of benzene.

The mixture of the two solutions is refluxed for 2 hours.

This reaction gives a yield of only 0.5% of allyl thiosulfate, which is identified according to the method described below, by 1% disulfide and 99% monosulfide.

EXAMPLE II

The procedure of Example I is followed, except that 4 mole percent of trimethylbenzylammonium chloride, calculated on the halide, is added as a catalyst.

After refluxing for 2 hours a 100% yield of thiosulfate is obtained which could be identified by the formation of 100% dialkyltrisulfide. After extraction by the conventional method the yield of the two steps (formation of $RSSO_3^-$ and conversion into trisulfide) is 93% by weight.

EXAMPLE III

A solution of 1.2 equivalents of sodium thiosulfate in 0.15 liter of demineralized or distilled water is prepared.

In a separate operation 1 equivalent of benzyl chloride is dissolved in 0.3 liter of benzene.

After refluxing for 2 hours a 5% yield (by weight) of benzyl thiosulfate is obtained; 80% of the benzyl chloride did not react; and the analysis carried out for identification of the formation of thiosulfate gives 10% monosulfide and 10% disulfide.

EXAMPLE IV

The same procedure is used as in Example III, except that 4% trimethylbenzylammonium is added as a catalyst. After refluxing for 2 hours a 77% yield of benzyl thiosulfate is obtained. 23% of the benzyl chloride did not react.

During the identification process there are formed
8.7% tetrasulfide
52.2% trisulfide
32.5% disulfide
0% monosulfide
with 6.6% unreacted benzyl chloride remaining.

EXAMPLE V

The same procedure is used as in Example IV, except that the mixture is refluxed for 4 hours. All the benzyl chloride reacts and a 98% yield of benzyl thiosulfate is obtained.

During the identification process there are formed
2% tetrasulfide
94% trisulfide
4% disulfide
0% monosulfide.

The yield of the two steps after extraction is 91% by weight.

EXAMPLE VI

The same procedure is used as in Example V, except that trimethylbenzylammonium hydroxide is used. A 62% yield of benzyl thiosulfate is obtained.

EXAMPLE VII

The same procedure is used as in Example VI, except that the refluxing time is reduced to 2 hours and the amount of catalyst increased to 8%. The yield of benzyl thiosulfate is 84.6%.

During the identification process there are formed
0% tetrasulfide
69.2% trisulfide
30.8% disulfide
0% monosulfide.

EXAMPLE VIII

The same procedure is used as in Example V, with the same proportions of benzyl chloride and sodium thiosulfate, but with the addition of 4% ethanoltrimethylammonium chloride (choline chloride).

After refluxing for 4 hours a 93.25% yield of benzyl thiosulfate is obtained, with 6.75% of unreacted benzyl chloride remaining.

During the identification process there are formed
0% tetrasulfide
86.5% trisulfide
13.5% disulfide
0% monosulfide.

The yield of the two steps after extraction is 95% by weight.

EXAMPLE IX

The same procedure is used as in Example V, except that 4% tributylhexadecylphosphonium bromide is added as the catalyst.

A 10.5% yield of benzyl thiosulfate is obtained.

During the process for identification of the thiosulfate there are formed:
0% tetrasulfide
1% trisulfide
20% disulfide
79% monosulfide.

EXAMPLE X

The same procedure is used as in Example IX, except that 4% dimethylbenzyldodecylammonium chloride is used.

A 48% yield of benzyl thiosulfate is obtained.

During the identification process for thiosulfate there are formed
0% tetrasulfide
7% trisulfide
83% disulfide
10% monosulfide.

EXAMPLE XI

The same procedure is used as in Examples V, VI, VIII, IX and X above, except that 5 g of ion exchange resin with grafted trimethylbenzylammonium groups (IRA 410 of Roehm and Haas) is used.

The yield of benzyl thiosulfate is 53.2%.

During the identification process there are formed
Traces of tetrasulfide
22% trisulfide
62.4% disulfide
11% monosulfide.

EXAMPLES XII AND XIII

The starting material is a solution of 1 equivalent of butyl chloride in 0.2 l of toluene, using 4 mole percent of trimethylbenzylammonium chloride as the catalyst. It is noted that no reaction takes place after refluxing for 4 hours, while after refluxing for 24 hours a 61.75% yield of butyl thiosulfate is obtained. During the identification process there are formed
0% tetrasulfide
23.5% trisulfide
76.5% disulfide
0% monosulfide.

EXAMPLES XIV TO XVII

In these 4 examples the starting material is a solution of 1 equivalent of butyl bromide in 0.2 l of benzene, which is mixed with a solution of 1.2 equivalents of sodium thiosulfate in water, and the mixture is refluxed for 24 hours in the presence of 4% of catalysts which are different for each example:

Example XIV: Trimethylbenzylammonium chloride
Example XV: Dimethylbenzyldodecylammonium chloride
Example XVI: Trimethyldodecylammonium chloride
Example XVII: Choline.

The yields of butyl thiosulfate vary between 25% and 81.35%, as can be seen in Table I, and it is noted that choline is the best catalyst. The amounts of sulfides formed during the identification process are also given in Table I.

For Example XVII the yield of the two steps after extraction is 76.5% by weight.

EXAMPLES XVIII TO XX

In these 3 examples the starting material is hexadecyl bromide or cetyl bromide dissolved in benzene, which is mixed with an aqueous solution of thiosulfate, as in the above examples.

No reaction takes place in the absence of catalyst, even after refluxing for 24 hours (Example XVIII).

In the presence of 4 mole percent of dimethylbenzyldodecylammonium and after 24 hours of reflux the yield of cetyl thiosulfate is 13.5% (Example XIX).

In the presence of 4% tributyl hexadecylphosphonium bromide a 25% yield is attained (Example XX).

EXAMPLE XXI

The starting material is a solution of ethyl bromoacetate in 0.2 l of benzene, which is reacted with an aqueous solution of sodium thiosulfate in the proportions indicated above.

The catalyst is tetrabutylammonium, added in an amount of 4% by weight. After refluxing for 24 hours, a 65% yield (by weight) of ethyl acetate thiosulfate is obtained.

EXAMPLE XXII

A solution of 1 equivalent of 1,4-dichloro-2-butene in 0.15 l of benzene is reacted with an aqueous solution of 2.4 equivalents of thiosulfate in 0.3 liter of water. 8 mole percent (calculated on the dihalide) of choline is added, and the mixture boiled for 4 hours. To identify the dithiosulfate formed the reaction with thiophenol is used, according to the following scheme:

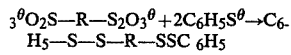
$3^\theta O_2S-R-S_2O_3^\theta + 2C_6H_5S^\theta \rightarrow C_6H_5-S-S-R-SSC_6H_5$ The above disulfide is identified by mass spectrography.

In this example the mass spectrography indicates the formation of the disulfide only, without monosulfide; in other words, a 100% yield of butenyl dithiosulfate has formed (see Table II).

EXAMPLE XXIII

The same procedure is used as in Example XXII, starting with 1 equivalent of p-xylenyl dichloride. After refluxing for 4 hours in the presence of 8 mole percent of choline, a 95% yield of dithiosulfate is obtained, which is identified as above.

| Halide | Catalyst | T in Hours | % Catalyst | Yield of Thiosulfate |
|--------|----------|------------|------------|----------------------|

CHOICE OF PHASE TRANSFER AGENT

Although the use of tetraalkyl phosphonium compounds is possible, preference is given to the ammonium compounds which give the best results.

For halides containing between 2 and 7 carbon atoms a catalyst having between 5 and 10 carbon atoms is chosen.

For reactive halides (allyl halides, benzyl halides) for which a reaction time of 4 hours is sufficient, one of the ammonium substituents may be a benzyl group; for alkyl halides a reaction time of 24 hours is required, hence a catalyst not containing a benzyl group is chosen, in order to avoid debenzylation of the catalyst.

For all these halides the use of choline chloride is recommended. With this catalyst the use of an aromatic solvent is recommended, inasmuch as choline chloride is sparingly soluble in straight-chain or cyclic solvents.

For halides having more than 7 carbon atoms a catalyst containing between 15 and 30 carbon atoms is chosen. For these halides the reaction time is at least 24 hours with 4% catalyst. Catalysts comprising a benzyl group are avoided for the same reasons as above.

The conventional phase transfer agents may be replaced with other compounds, such as:

BETAINES

$R'_3 - \overset{\oplus}{M} - (CH_2)_n CO_2H, X^\ominus$ where M is a N or a P; X is Cl or Br.

EXAMPLE

$(C_{12}H_{25})_3 \overset{\oplus}{N} - CH_2 - CO_2H, Br^\ominus$

AMINO ACIDS

$R'_2 - N(CH_2)_n CO_2H$ such as

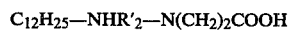
$C_{12}H_{25} - NHR'_2 - N(CH_2)_2 COOH$

OXYETHYLATED OR OXYPROPYLATED ETHERS OR AMINES

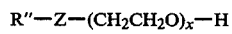
$R'' - Z - (CH_2CH_2O)_x - H$
or
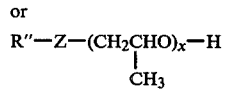
$R'' - Z - (CH_2CHO)_x - H$
            $|$
            $CH_3$ where Z is O or NH or N—R"
such as

$C_{12}H_{25}O(CH_2CH_2O)_xH \quad 10 < x < 30$

ION EXCHANGE RESINS such as the cross-linked polystyrene resins on which quaternary ammonium groups are grafted. As an example, commercial resins such as Amberlite IRA 410, may be used. In this case a three-phase catalysis takes place.

IDENTIFICATION OF THE ALKYL OR ARALKYL THIOSULFATES

There are three possible methods for determining the percent of $R-SSO_3^\theta$ formed:

1. Isolation of the $RSSO_3^\theta$: This is a difficult operation because $RSSO_3^\theta$, which is water-soluble, is in the presence of inorganic compounds (NaCl and excess $S_2O_3^{--}$).

2. Extraction of the unreacted RX: This method has a major drawback in the case of volatile halides, namely the risk of underestimating the real amount of unreacted RX.

3. Carrying out a second step which will transform $RSSO_3^\theta$ and the halide RX into readily identifiable organic compounds.

It was decided to carry out the reaction with $Na_2S$ which will transform the products present ($R-SSO_3^\theta$ and R—X) into trisulfide, disulfide and monosulfide according to the following reactions:

(1) FORMATION OF TRISULFIDE

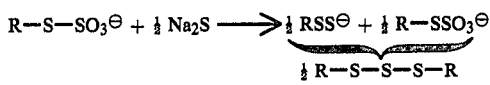

(2) FORMATION OF MONOSULFIDE

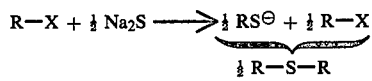

(3) FORMATION OF DISULFIDE

First possibility

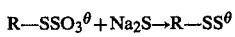

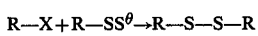

Second possibility:

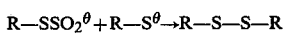

The trisulfide is formed from $R\!-\!SSO_3^\ominus$. Both of the R groups forming this compound originate from $R\!-\!SSO_3^\ominus$ formed in the first step.

The monosulfide and disulfide both originate from the halide that has not reacted at the end of the first step. Both R groups present in the monosulfide originate from the halide. On the other hand one of the R groups of the disulfide formed according to Possibility 1 or 2 originates from the halide, and the other R group from the $R\!-\!SOO_3^\ominus$.

The percentage of $RSSO_3^\ominus$ formed during the first step is obtained by adding one half of the amount of the obtained disulfide to the amount of trisulfide formed. It is this percentage that defines the degree of advance of the first step, i.e. the formation of the alkyl thiosulfate.

Tetrasulfide, if any, is always present in a very small quantity only. It may originate from secondary reactions with the trisulfide which has already formed.

Finally it has been verified that the monosulfide does in fact originate from the reaction of $Na_2S$ and $R\!-\!X$.

It should be pointed out that the reaction of $Na_2S$ with $R\!-\!X$ is accelerated by phase transfer agents containing more than 15 carbon atoms, as has been reported by Tozzi and Cassandrini (A. Tozzi and P. Cassandrini, Chimosa Chimica Org. Spa., German Patent 2,513,805). Transfer agents containing less than 12 carbon atoms have little effect on this reaction. Indeed, one mole of benzyl chloride made to react with ½ mole of $Na_2S$ in the presence of 0.04 mole of trimethylbenzylammonium chloride in benzene under reflux for 1½ hours leads to 20% monosulfide and 80% benzyl chloride.

Likewise the disulfide does, in fact, originate from the reaction of $R\!-\!SS^\ominus$ with unreacted chloride. Indeed, after reacting $S_2O_3^=$ with benzyl chloride under conditions where the degree of advance of the first step is 77%, 32.5% of disulfide and 52.2% of trisulfide are isolated.

Under identical operating conditions but by extracting the unreacted chloride at the end of the first step, 10% disulfide and 90% trisulfide are obtained. The possibility that the disulfide originates from the trisulfide as a result of a reaction between the latter and sodium sulfide (which forms during the identification step), as observed by Milligan, has been ruled out.

As a matter of fact a sample of pure trisulfide, reacted for 1½ hours at 70° C. with sodium sulfide in the presence of a phase transfer agent, did not proceed toward the formation of disulfide. On the other hand the same reaction carried out at 90° led to 20% disulfide, and the same reaction carried out for 4 hours at 70° C. led to 100% disulfide. These results indicate that with a reflux time of 1½ hours in the identification step, the relative proportions of $S_3$ and $S_2$ reflect well the degree of advance of the first step.

The relative proportions of monosulfide, disulfide, trisulfide and unreacted halide are determined by nuclear magnetic resonance.

For each of these products the signal of the hydrogen atoms in alpha position to the sulfur or of the halogen atom is displaced differently, owing to the different electronic environment.

For example in the case

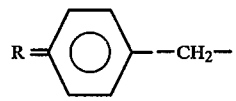

the chemical shifts of these hydrogens relative to tetramethylsilane are as follows:

| | |
|---|---|
| Monosulfide | $\delta = 3.46$ |
| Disulfide | $\delta = 3.50$ |
| Trisulfide | $\delta = 3.90$ |
| Tetrasulfide | $\delta = 4.00$ |
| Benzyl chloride | $\delta = 4.40$ |

The presence or absence of one of these compounds is verified by mass spectrometry of a sample of the mixture.

The method of determination consists in carrying out the synthesis of the sulfides in the following manner:

0.5 equivalent of sodium sulfide is dissolved in 0.3 to 0.5 liter of demineralized water while a stream of nitrogen is bubbled through during the dissolution. This solution is added in one portion to the above mixture, and refluxed for 1.5 hours.

An amount of methylene chloride required in order that the organic phase have a density of more than 1 is added. After decanting, the aqueous phase is twice extracted with methylene chloride, the combined organic phases are twice washed with water to eliminate the transfer agent (the lipophilic transfer agents cannot be eliminated completely from the organic phase). After percolation over a drying agent ($Na_2SO_4$) the solvent is evaporated, the material yield of the two steps after extraction ($R\!-\!Cl \rightarrow RSSO_3^-$ and identification by conversion into sulfides) being comprised between 75% and 100%.

TABLE I

| EX | Halide | Catalyst R | Catalyst X | t (h) | % Catalyst | Unreacted RX | $RS_4R$ % | $RS_3R$ % | $RS_2R$ % | RSR % | % $R-SSO_3$ Formed |
|---|---|---|---|---|---|---|---|---|---|---|---|
| 1 | $CH_2=CH-CH_2-$ | Cl | $\phi\text{-}CH_2\text{-}N^{\oplus}(CH_3)_3Cl^{\ominus}$ | 2 | 0 | 0 | 0 | 0 | ≃1 | ≃99 | ≃05 |
| 2 | | | | 2 | 4 | 0 | 0 | 100 | 0 | 0 | 100 |
| 3 | 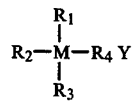$-CH_2-$ | Cl | $\phi\text{-}CH_2\text{-}N^{\oplus}-(CH_3)_3Cl^{\ominus}$ | 2 | 0 | 80 | 0 | 0 | 10 | 10 | 5 |
| 4 | | | " | 2 | 4 | 6,6 | 8,7 | 52,2 | 32,5 | 0 | 77 |
| 5 | | | " | 4 | 4 | 0 | 2 | 94 | 4 | 0 | 98 |
| 6 | | | $\phi\text{-}CH_2\text{-}N^{\oplus}-(CH_3)_3\overset{\ominus}{O}H$ | 4 | 4 | 0 | 4,5 | 19,5 | 76 | 0 | 62 |
| 7 | | | " | 2 | 8 | 0 | 0 | 69,2 | 30,8 | 0 | 84,6 |
| 8 | | | $HO-CH_2-CH_2-N(CH_3)_3Cl^{\ominus}$ | 4 | 4 | 0 | 0 | 86,5 | 13,5 | 0 | 93,25 |
| 9 | | | $C_{16}H_{33}P^{\oplus}(C_4H_9)_3Br^{\ominus}$ | 4 | 4 | 0 | 0 | 1 | 20 | 79 | 10,5 |
| 10 | | | $C_{12}H_{25}N{\overset{\oplus}{\underset{CH_2\phi}{\diagdown}}}(CH_3)_2Cl^{\ominus}$ | 4 | 4 | 0 | 0 | 7 | 83 | 10 | 48,3 |
| 11 | | | $-\phi\text{-}CH_2\overset{\oplus}{-}N(CH_3)_3Cl^{\ominus}$ resin | 4 | 5g | 4,6 | 0 | 22 | 62,4 | 11 | 53,2 |
| 12 | $CH_3-(CH_2)_3-$ | Cl | $\phi\text{-}CH_2\overset{\oplus}{-}N-(CH_3)_3Cl^{\ominus}$ | 4 | 4 | 100 | 0 | 0 | 0 | 0 | 0 |
| 13 | | | " | 24 | 4 | 0 | 0 | 23,5 | 76,5 | 0 | 61,75 |
| 14 | $CH_3-(CH_2)_3-$ | Br | $\phi CH_2\overset{\oplus}{-}N-(CH_3)_3Cl^{\ominus}$ | 24 | 4 | 0 | 0 | 16,5 | 83,5 | 0 | 58,2 |
| 15 | | | $C_{12}H_{25}-N{\overset{\oplus}{\underset{CH_2\phi}{\diagdown}}}(CH_3)_2Cl^{\ominus}$ | 24 | 4 | 0 | 0 | 68 | 32 | | 34 |
| 16 | | | $C_{12}H_{25}\overset{\oplus}{-}N-(CH_3)_3Cl^{\ominus}$ | 24 | 4 | 0 | 0 | 50 | 50 | | 25 |
| 17 | | | $HO-CH_2-CH_2-\overset{\oplus}{N}-(CH_3)_3Cl^{\ominus}$ Choline | 24 | 4 | 0 | 8 | 62,7 | 37,3 | 0 | 81,35 |
| 18 | $CH_3(CH_2)_{15}-$ | Br | | 24 | 0 | 100 | 0 | 0 | 0 | 0 | 0 |
| 19 | | | $CH_{12}H_{25}-N{\overset{\oplus}{\underset{CH_2-\phi}{\diagdown}}}(CH_3)_2Cl^{\ominus}$ | 24 | 4 | 24 | 0 | 1 | 25 | 50 | 13,5 |
| 20 | | | $C_{16}H_{33}P^{\oplus}-(C_4H_9)_3Br^{\ominus}$ | 24 | 4 | 30 | 0 | 0 | 50 | 20 | 25 |
| 21 | $EtO-\underset{\underset{O}{\|}}{C}-CH_2$ | Br | $Bu_4-N^{\oplus}, Cl^{\ominus}$ | 24 | 4 | 0 | 0 | 50 | 30 | 20 | 65 |

What is claimed is:

1. In a process for preparing alkyl, alkaryl, acylester or aralkyl thiosulfates by reaction of an alkyl, alkylene, acylester or aralkyl halide with thiosulfate, the improvement which comprises reacting an alkyl, alkylene, acylester or aralkyl halide in an organic solvent, for said halide; immiscible with water, with an aqueous solution of the thiosulfate, in the presence of from 0.5 to 10 moles percent, based on the moles of said halide, of a phase transfer agent of the formula $$\begin{array}{c} R_1 \\ | \\ R_2-M-R_4\ Y \\ | \\ R_3 \end{array}$$

wherein M is N or P, Y is halide or OH and $R_1$, $R_2$, $R_3$ and $R_4$ are independently aryl, alkaryl, alkyl, hydroxy alkyl, and carboxy alkyl, wherein not more than one R can be hydroxy alkyl and carboxy alkyl and the total number of carbon atoms in $R_1$, $R_2$, $R_3$ and $R_4$ is from 5 to 40, and ion exchange resins containing grafted quarternary ammonium groups of the formula $$\begin{array}{c} R_1 \\ | \\ R_2-M-R_4\ Y \\ | \\ R_3 \end{array}$$

wherein $R_1$, $R_2$, $R_3$, $R_4$ and Y are as defined herebefore, which permits the thiosulfate ion to pass from the aqueous phase to the organic phase wherein the reaction occurs.

2. A process according to claim 1 wherein said molar proportion varies from 2 to 10 mole percent.

3. A process according to claim 1, wherein the alkyl or aralkyl halide contains up to 25 carbon atoms.

4. A process according to claim 1 wherein the halide is represented by the formula RX wherein R is selected from the group consisting of alkylene, alkyl and aralkyl radicals and X is a halogen.

5. A process according to claim 4 wherein the halogen is chlorine or bromine.

6. A process according to claim 1 wherein the halide is represented by the formula $$X-R-X$$

wherein R is a radical selected from the group consisting of radicals derived from alkylene, alkyl and aralkyl radicals by the loss of a hydrogen atom and X is chlorine or bromine.

7. A process according to claim 1 wherein the phase transfer agent is selected from the group consisting of alkylarylammonium halides and hydroxides and phosphonium halides and hydroxides and ion exchange resins containing grafted quaternary ammonium groups.

8. A process according to claim 1 wherein, for the synthesis of thiosulfates whose organic group contains 2 to 7 carbon atoms, a phase transfer agent comprising an ammonium group containing 5 to 20 carbon atoms are used.

9. A process according to claim 8 wherein the phase transfer agent contains 5 to 10 carbon atoms.

10. A process according to claim 1 wherein, for the synthesis of thiosulfates whose organic group contains more than 7 carbon atoms, a phase transfer agent comprising an ammonium group containing 10 to 40 carbon atoms, is used.

11. A process according to claim 10, wherein the phase transfer agent contains 15 to 30 carbon atoms.

12. A process according to claim 1 wherein the reaction is conducted under reflux for 2 to 24 hours.

13. The process of claim 1, wherein the phase transfer agent is selected from the group consisting of trimethylbenzyl ammonium chloride, choline chloride, tributylhexadecylphosphonium bromide, dimethylbenzyldodecylammonium chloride, trimethyldodecylammonium chloride, tetrabutylammonium chloride, triethylbenzylammonium chloride, tricaprylmethylammonium chloride, trihexylmethylammonium chloride, cetyltrimethylammonium chloride, dimethylphenyldodecylammonium chloride and ion exchange resins containing grafted quarterny ammonium groups.

14. The process of claim 1, wherein the phase transfer agent is chlorine chloride.

* * * * *

UNITED STATES PATENT OFFICE
CERTIFICATE OF CORRECTION

Patent No. 4,191,702       Dated March 4, 1980

Inventor(s) Gilbert Chapelet, et al

It is certified that error appears in the above-identified patent and that said Letters Patent are hereby corrected as shown below:

Column 1, line 9: "$RX+S_2O_3^{--}$" should be --$RX+S_2O_3^{=}$--.

line 25: "$(S_2O_3^{--})$" should be --$(S_2O_3^{=})$--.

Column 2, line 29: "$S_2O_3^{--}$" should be --$S_2O_3^{=}$--.

Column 6, line 56: "$S_2O_3^{--})$" should be --$S_2O_3^{=}$--.

Columns 9-10, Table I, the last column heading:

" % R—$SSO_3$ Formed " should be -- % R-$SSO_3\ominus$ Formed --.

Table I, Ex. 1, last column: "05" should be --0,5--.

Signed and Sealed this

Fifth Day of August 1980

[SEAL]

Attest:

SIDNEY A. DIAMOND

Attesting Officer       Commissioner of Patents and Trademarks